(12) United States Patent
Yamaguchi et al.

(10) Patent No.: US 9,222,206 B2
(45) Date of Patent: Dec. 29, 2015

(54) NONWOVEN FABRIC AND METHOD FOR MANUFACTURING SAME

(75) Inventors: Masashi Yamaguchi, Kanonji (JP); Satoshi Mizutani, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 996 days.

(21) Appl. No.: 13/389,464

(22) PCT Filed: Jun. 21, 2010

(86) PCT No.: PCT/JP2010/060418
§ 371 (c)(1),
(2), (4) Date: Feb. 8, 2012

(87) PCT Pub. No.: WO2011/018921
PCT Pub. Date: Feb. 17, 2011

(65) Prior Publication Data
US 2012/0141742 A1   Jun. 7, 2012

(30) Foreign Application Priority Data
Aug. 11, 2009 (JP) ................................ 2009-186885

(51) Int. Cl.
*B32B 3/28* (2006.01)
*D04H 1/541* (2012.01)
*D04H 3/04* (2012.01)
(Continued)

(52) U.S. Cl.
CPC ............ *D04H 1/54* (2013.01); *A61F 13/51108* (2013.01); *D04H 1/4291* (2013.01); *D04H 1/435* (2013.01); *D04H 1/485* (2013.01); *D04H 1/495* (2013.01); *D04H 1/541* (2013.01); *D04H 1/542* (2013.01); *A61F 13/51121* (2013.01); *D06C 3/00* (2013.01); *Y10T 428/24603* (2015.01); *Y10T 428/24694* (2015.01); *Y10T 428/24942* (2015.01)

(58) Field of Classification Search
CPC combination set(s) only.
See application file for complete search history.

(56) References Cited

U.S. PATENT DOCUMENTS

2006/0286343 A1   12/2006   Curro et al.
2007/0298667 A1*  12/2007   Noda et al. ...................... 442/50
(Continued)

FOREIGN PATENT DOCUMENTS

EP     792629 A2    9/1997
EP     2034066 A1   3/2009
(Continued)

OTHER PUBLICATIONS

Extended European Search Report issued Nov. 28, 2013, corresponds to European patent application No. 10808105.0.
(Continued)

*Primary Examiner* — Donald J Loney
(74) *Attorney, Agent, or Firm* — Hauptman Ham, LLP (57) ABSTRACT

A nonwoven fabric facilitating permeation of loose passage. A nonwoven fabric is formed of short fibers of thermoplastic synthetic resin fused together. The nonwoven fabric is formed on a top side thereof with ridges and troughs undulating in a width direction and extending in parallel to one another in a length direction. When the nonwoven fabric is placed on a horizontal plane with the back side put in contact with the horizontal plate, highly void regions are formed between the back side and the horizontal plane. In the vicinity of apices of the respective ridges, the short fibers slope down so as to extend in a thickness direction of the nonwoven fabric.

7 Claims, 8 Drawing Sheets

(51) Int. Cl.
*D04H 1/54* (2012.01)
*D04H 1/4291* (2012.01)
*D04H 1/435* (2012.01)
*D04H 1/485* (2012.01)
*D04H 1/495* (2012.01)
*D04H 1/542* (2012.01)
*D06C 3/00* (2006.01)
*A61F 13/511* (2006.01)

(56) References Cited

U.S. PATENT DOCUMENTS

2007/0298671 A1 12/2007 Noda et al.
2010/0191207 A1 7/2010 Oba et al.

FOREIGN PATENT DOCUMENTS

| EP | 2034069 A1 | 3/2009 |
| EP | 2161361 A1 | 3/2010 |
| JP | 2008025080 A | 2/2008 |
| JP | 2009030218 A | 2/2009 |
| JP | 2009062650 A | 3/2009 |

OTHER PUBLICATIONS

International Search Report and Written Opinion for PCT/JP2010/060418 dated Aug. 31, 2010.

* cited by examiner

NONWOVEN FABRIC AND METHOD FOR MANUFACTURING SAME

RELATED APPLICATIONS

The present application is a National Phase of International Application Number PCT/JP2010/060418, filed Jun. 21, 2010 and claims priority from Japanese Application Number 2009-186885, filed Aug. 11, 2009.

TECHNICAL FIELD

This invention relates to nonwoven fabrics and methods for manufacturing the same and, more particularly, to nonwoven fabrics suitable to be used as a liquid-pervious topsheet of bodily fluid absorbent articles such as disposable diapers and methods for manufacturing the same.

BACKGROUND

Conventionally, it is known to cover absorbent structures in bodily fluid absorbent articles such as disposable diapers and sanitary napkins with liquid-pervious topsheets. It is also known to use nonwoven fabrics as the liquid-pervious topsheets and to use, in many cases, short fibers of thermoplastic synthetic resins as a material for the nonwoven fabrics. For example, a nonwoven fabric disclosed in JP2008-25080A (PTL 1) is suitable to be used as a topsheet. This nonwoven fabric is formed by ejecting hot air to a web formed of the short fibers of thermoplastic synthetic resin so that, in the machine direction, the ridges and the troughs may extend in parallel to one another and, in the cross direction orthogonal to the machine direction, these ridges and troughs may alternate.

CITATION LIST

Patent Literature

{PTL 1} JP 2008-25080 A

SUMMARY

Technical Problem

In the nonwoven fabric as has been exemplarily cited above, hot air is ejected from a plurality of nozzles arranged in the width direction of the web to form the regions of the web respectively lying immediately below the nozzles with the troughs and to form the regions of the web respectively lying between the adjacent ridges. In this regard, however, an apparent density in each of the ridges is higher than an apparent density in each of the troughs. If such nonwoven fabric is used as the topsheet in the disposable diaper, body waste having a low density such as loose passage is apt to stay in the ridges in which the apparent density is relatively high and it may be difficult for such body waste to permeate quickly the topsheet and to migrate toward the absorbent structure underlying the topsheet.

An object of the present invention is to improve the conventional nonwoven fabric so that the nonwoven fabric may facilitate loose passage to permeate the nonwoven fabric when this nonwoven fabric is used as the topsheet.

Solution to Problem

This invention includes a first aspect relating to a nonwoven fabric and a second aspect relating to a method for manufacturing the nonwoven fabric.

The first aspect of this invention relates to a nonwoven fabric including short fibers fused together, having a top side and a back side wherein the top side is formed with a plurality of ridges extending in parallel to one another in one direction and a plurality of troughs each defined between a pair of the adjacent ridges and extending in the one direction.

In the nonwoven fabric, the first aspect of this invention is as follows: from observation of a cross-section of the nonwoven fabric taken in a direction orthogonal to the one direction with the back side placed on a horizontal plane, it is demonstrated that highly void regions larger than interstices among the short fibers are formed between the back side of the ridges and the horizontal plane and the short fibers slope down to extending in a thickness direction of the nonwoven fabric at least in the vicinities of apices of the respective ridges.

According to one embodiment of the first aspect of this invention, in the cross section, an average value of crossing angles between a reference line passing an apex of each ridge perpendicularly to the horizontal plane and the short fibers is 75° or less.

According to another embodiment of the first aspect of this invention, in the cross section, an area ratio of void regions defined by a ratio of a sum of an area occupied by interstices among the short fibers in the cross section of the ridges and a cross-sectional area of the highly void regions to a sum of the cross-sectional area of the ridges and the cross-sectional area of the highly void regions is in a range of 3.5 to 25.0%.

According to still another embodiment of the first aspect of this invention, an elastic height recovery rate of the ridges as measured after the top side has been subjected to a load of 20 g/cm$^2$ for 3 minutes and then left in rest for 5 minutes is at least 85%.

According to yet another embodiment of the first aspect of this invention, the nonwoven fabric has a mass per unit area in a range of 10 to 80 g/m$^2$ and the short fibers have fineness in a range of 1 to 11 dtx, a fiber length in a range of 20 to 80 mm and treated to become hydrophilic.

According to further another embodiment of the first aspect of this invention, each of the short fibers is conjugate fibers formed from two kinds of thermoplastic synthetic resins respectively have different fusion temperatures and the short fibers are fused together through the intermediary of the one having the fusion temperature lower than that of the other in these two kinds of thermoplastic synthetic resins.

The second aspect of this invention relates to a method for manufacturing the nonwoven fabric defined by Claim 1, including:

(1) a first step, as a preliminary treating step, of placing web formed from short fibers of thermoplastic synthetic resin and having a top side and a back side on air-permeable support means to feed the web in a machine direction under suction effect of first suction means exerted from below the support means and ejecting first air jets preheated and having an airflow rate three times or less of a suction volume of the first suction means to the web in a thickness direction from the top side to the back side so as to compress the web in the thickness direction and simultaneously to fuse the short fibers together; and (2) a second step of feeding the web placed on the support means further in the machine direction under suction effect of second suction means exerted from below the support means and ejecting second air jets having an airflow rate three times or more of a suction volume of the second suction means from a plurality of nozzles arranged in a direction orthogonal to the machine direction at required intervals to the web in the thickness direction from the top side to the back side so that the airflow rate of the second air jets may be partially reflected on the support means and thereby forming a plurality of ridges extending in the machine direction in parallel to one another, a plurality of troughs defined between the adjacent ridges and extending in the machine direction and, between the back side in the ridges and the support means, highly void regions larger than interstices among the short fibers in the ridges.

Advantageous Effects of Invention

In the nonwoven fabric according to this invention, the fibers slope down in the thickness direction of the nonwoven fabric in the vicinities of the apices of the respective ridges and, in addition, the respective ridges include the highly void regions on the back side. As an advantageous consequence, body waste having high viscosity such as loose passage may smoothly migrate downward from the apices of the respective ridges and/or permeate the ridges.

DESCRIPTION OF EMBODIMENTS

Details of a nonwoven fabric and a method for manufacturing the same will be described hereunder with reference to the accompanying drawings.

Figure 1:
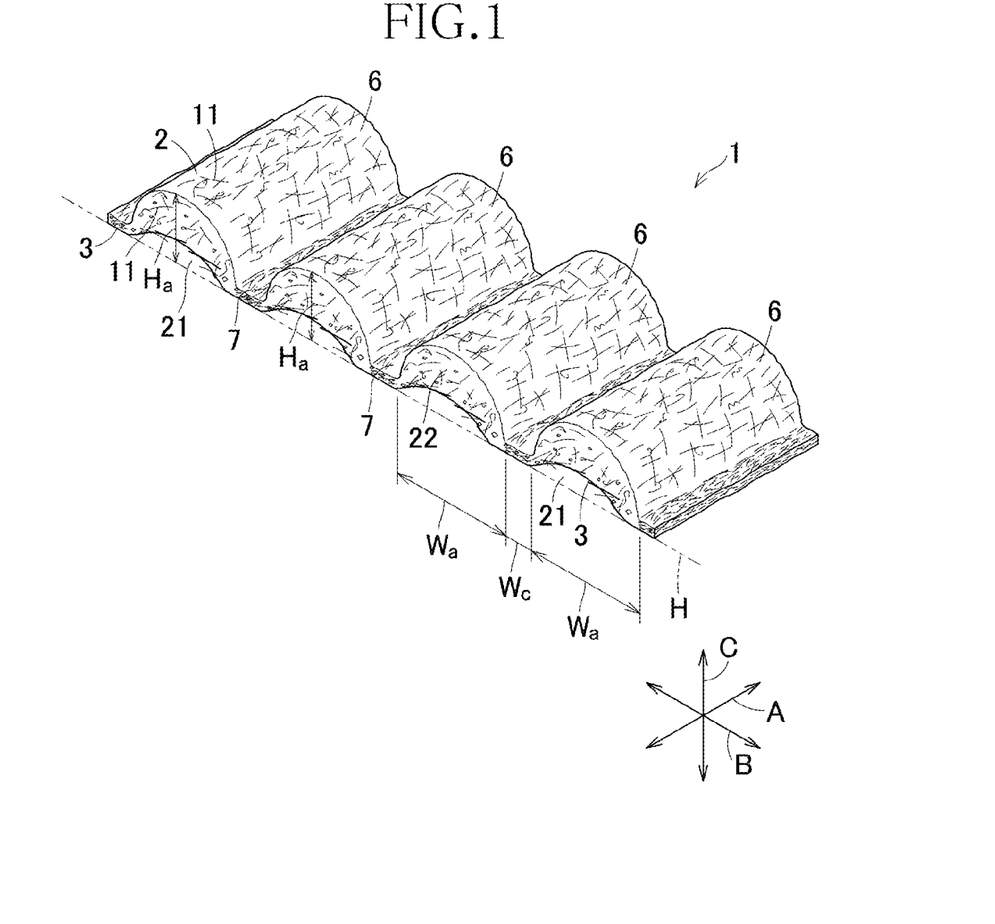
FIG. 1 A partial perspective view of a nonwoven fabric.
Figure 2:
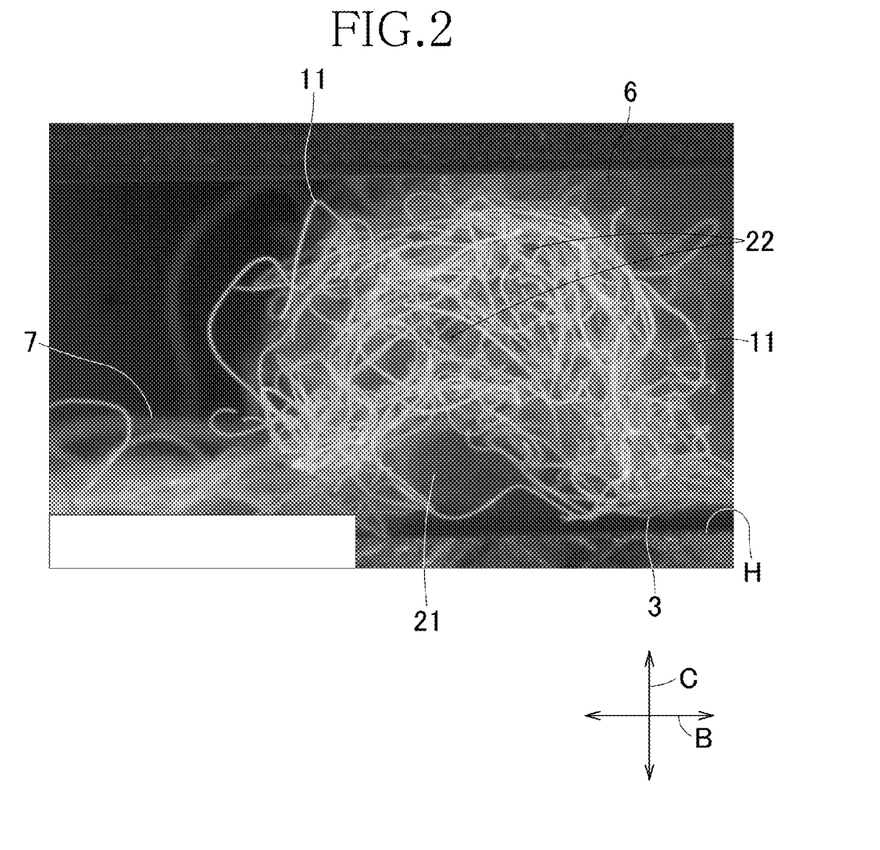
FIG. 2 A photograph showing cross-section of raised ridge of the nonwoven fabric taken in cross direction.

FIG. 1 is a perspective view schematically illustrating a part of a nonwoven fabric 1 and FIG. 2 is a photograph of 50-fold magnifications showing a part of a cross-section of the nonwoven fabric 1. The nonwoven fabric 1 has a length direction, a width direction and a thickness direction being orthogonal to one another as respectively indicated by double-headed arrows A, B and C and, in the thickness direction C, the nonwoven fabric 1 includes a top side 2 and a back side 3 opposite to the top side 2. The nonwoven fabric 1 is formed on the top side 2 thereof with a plurality of ridges 6 and a plurality of troughs 7 extending in parallel to one another in the length direction A and alternating in the width direction B so as to define undulation. The individual ridges 6 have a substantially uniform height $H_a$ as measured from a horizontal surface H in the thickness direction C.

The nonwoven fabric 1 is formed from short fibers 11 of a thermoplastic synthetic resin preferably each having a fineness in a range of 1 to 11 dtex and a fiber length in a range of 20 to 80 mm. Specifically, these short fibers 11 are fused together under the effect of hot air jets to form the nonwoven fabric 1. The nonwoven fabric 1 is suitable to be used as a liquid-pervious topsheet in the bodily fluid absorbent wearing article such as a disposable diaper or a sanitary napkin and, for such intended purpose, the nonwoven fabric 1 preferably has a mass per unit area in a range of 10 to 80 g/m² and the short fibers 11 preferably have been pretreated to become hydrophilic. On the top side 2 of the nonwoven fabric 1, each of a plurality of troughs 7 have a dimension $W_c$ in the width direction B in a range of 0.4 to 2 mm and each of a plurality of ridges 6 have a dimension $W_a$ in the width direction B in a range of 2 to 5 mm. The respective ridges 6 have a height dimension $H_a$ in a range of 1 to 5 mm. The troughs 7 preferably lie at a level 0.7 to 2.5 mm lower than the height $H_a$. To facilitate the individual short fibers 11 to be fused together and to assure the nonwoven fabric 1 to be elastically contractible in the thickness direction C, the short fibers 11 are preferably conjugate fibers each composed of two types of synthetic resins having different fusion temperatures so that the synthetic resins having the lower fusion temperature may be fused in advance of the synthetic resins having the higher fusion temperature and fusing bonded to the latter. As such synthetic resin combinations, for example, combinations of polyethylene/polyester and polyethylene/polypropylene are publicly or widely known. The conjugate fibers may be the core-in-sheath type or the side-by-side type. The core-in-sheath type conjugate fibers may be concentric type or eccentric type. These conjugate fibers are preferably thermally or mechanically treated to crimp them. The short fibers 11 in this invention are not limited to the conjugate fibers but it is possible to use, for example, the ones formed from polyethylene, polypropylene, nylon or polyester.

Figure 3:
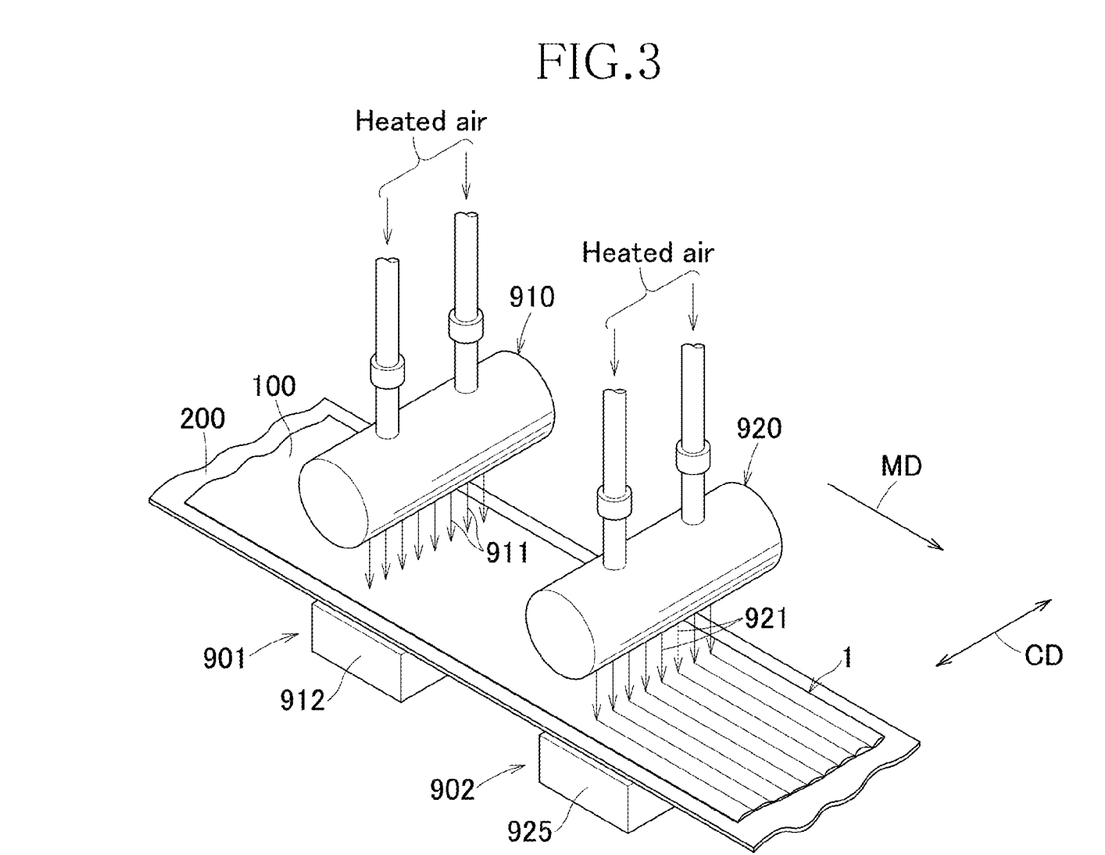
FIG. 3 A diagram illustrating a part of manufacturing process for the nonwoven fabric.
Figure 4:
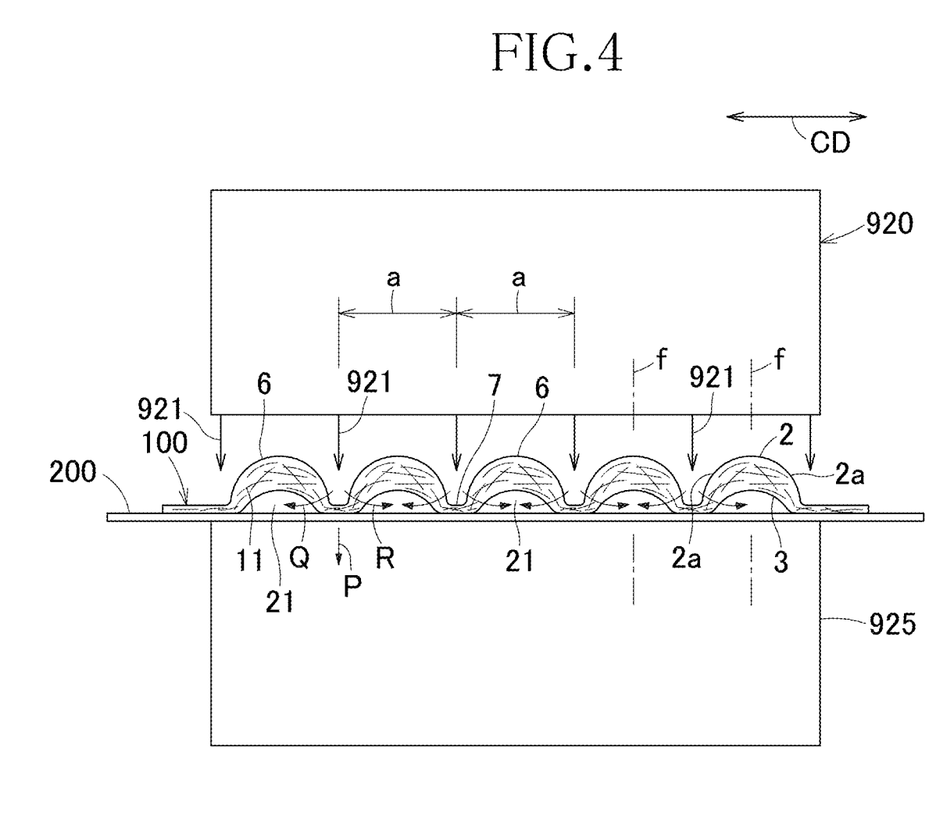
FIG. 4 A front view of a second manifold of nozzles.

FIGS. 3 and 4 are, respectively, a diagram illustrating part of a manufacturing process for the nonwoven fabric 1 in FIGS. 1 and 2 and a front view of a second manifold of nozzles 920 in FIG. 3. Referring to FIG. 3, a carded web 100 formed from the short fibers 11 and having a mass per unit area in a range of 10 to 80 g/m² is placed on a running belt 200 serving as supporting means and having air-permeability in the thickness direction and runs in a machine direction MD. As the running belt 200, a mesh plate having openings, for example, of 30 meshes or more may be used. In the machine direction MD, the process includes a first step 901 which is a preliminary treatment step adapted to compress the carded web 100 in its thickness direction to fuse the short fibers 11 together and thereby to stabilize the formation of the carded web 100 and a second step 902 adapted to form the carded web 100 preliminarily treated in this manner with the ridges 6. In the first step 901, the carded web 100 is subjected to blast of heated first air jets (streams) 911 from the first manifold of nozzles 910 and the first air jets (streams) 911 are sucked by a first suction box 912 through the belt 200. An airflow rate of the first air jets 911 is regulated to three times or less of intake volume of the first suction box 912. Temperature of the first air jets 911 is set to a temperature at which the short fibers 11 can be sufficiently fused together.

In the second step 902 illustrated in FIG. 3, the carded web 100 having been treated in the first step 901 is subjected to a plurality of heated second air jets 921 from a second manifold of nozzles 920. The second air jets 921 partially heave the carded web 100 having its formation stabilized in the first step 901 in a cross direction CD so that the carded web 100 may be formed along portions corresponding to spaces defined between respective pairs of the adjacent second air jets with the ridges 6. To achieve this, airflow rate from the second manifold 920 is set to at least three times of the intake volume of a second suction box 925.

In the second manifold 920 illustrated in FIG. 4, the second air jets 921 are ejected down toward the carded web 100 from a plurality of nozzles (not shown) arranged at a required center-to-center distance a in the cross direction CD. When the airflow rate of the second air jets begins to exceed the intake volume of the second suction box 925, the second air jets more and more tend to be divided into a flow P sucked into the second suction box 925 through the belt 200 and flows Q, R headed along the belt 200 toward both sides of the cross direction CD (See FIG. 4) and, when the airflow rate increases to exceed three times of the intake volume of the second suction box 925, each formation of the ridges 6, the troughs 7 and highly void regions 21 progressively becomes marked under the effect of the second air jets 921. Considering such tendency, it is preferred to use an air-permeable belt of 30 meshes or more or to use an air-permeable aperture plate of an open area ratio in a range of 5 to 30% in which nonporous portions defined between each pair of the adjacent apertures has a width in a range of 1 to 20 mm and to set the airflow rate from the second manifold 920 to three times or more of the intake volume of the second suction box 925 in order that these ridges 6, the troughs 7 and the highly void regions 21 are reliably formed in the second step 902.

Respective positions of the second air jets 921 at the center-to-center distances a in the cross direction CD correspond to positions of the troughs 7 in the nonwoven fabric 1 illustrated in FIG. 1. In the carded web 100, portions of the short fibers 11 lying immediately below the respective second air jets 921 are migrated toward both sides in the cross direction CD to participate in the formation of the ridges 6 while the short fibers remaining immediately below the second air jets 921 form the respective troughs 7. In addition to such migration, portions of the short fibers lying between respective pairs of the adjacent second air jets 921 migrate in the cross direction CD toward respective center lines f (See FIG. 4) bisecting the respective center-to-center distances a to form the ridges 6. Constituent flows Q, R of the second air jets 921 also function to drive upward the short fibers 11 having been horizontally laid in the form of the web 100 above the belt 200 along the center lines f so as to form relatively large highly void regions 21 (See FIG. 2) between the back sides of the respective ridges 6 and the belt 200. During the course in which the web 100 forms the ridges 6 and the highly void regions 21 in this manner, the short fibers 11 having been horizontally laid upstream of the second step 902 change a direction thereof so that the short fibers may be vertically oriented along sloping top side sections 2a of the top sides 2 of the respective ridges 6. In the ridges 6 of the nonwoven fabric 1 containing such short fibers 11, a downward movement of urine and loose passage is facilitated and, when the nonwoven fabric 1 is used as a topsheet of a disposable diaper, movement of urine or loose passage to the absorbent structure covered with this nonwoven fabric is also facilitated.

According to the inventors' findings, assuming that a suction volume of the second suction box 925 is constant in the manufacturing process of the nonwoven fabric 1, a ratio of a void region area corresponding to a sum of a total area of the highly void regions 21 defined between the back sides 3 of the respective ridges 6 and the horizontal surface H in the cross-section illustrated in FIG. 2 and a total area of the interstices among the short fibers 11 in the ridges 6 to a sum of a total cross-sectional area of the ridges 6 and a total area of the highly void regions 21—which is referred to as area ratio of void regions in this invention—is apt to vary depending on an airflow rate of the second air jets 932 ejected from the second manifold 920. A method for measuring the area ratio of the void region will be described later. According to the inventors' additional findings, permeation time of artificial loose passage is apt to depend on the area ratio of the void regions. These findings were obtained from the measuring operation as follows: as the short fiber 11, concentric core-in-sheath conjugate fiber composed of polyethylene as the sheath and polyester as the core combined at a volumetric ratio of 6:4 was used. The conjugate fibers had a fineness of 2.6 dtex, a fiber length of 64 mm, 15 (fifteen) mechanical crimps per 25.4 mm and was previously treated to become hydrophilic. The carded web 100 was obtained by carding these short fibers 11 and mass per unit area thereof was 30 g/m². In the process illustrated in FIGS. 3 and 4, the first manifold 910 operated under the conditions as follows: nozzle diameter: 1 mm, center-to-center distance of the nozzles in the cross direction CD: 2 mm, distance between the nozzles and the carded web: 5 mm, temperature of the first air jets 911: 140° C., airflow rate of the first air jets 911: 3.3 L/min, suction rate of the first suction box 912: 5 m/sec. The second manifold 920 operated under the conditions as follows: nozzle diameter: 1 mm, center-to-center distance a of the nozzles in the cross direction CD: 4 mm, distance between the nozzles and the carded web: 5 mm, temperature of the second air jets 921: 180° C., airflow rate of the second air jets 921: 4.0 to 8.3 L/min, suction rate of the second suction box 925: 5 m/sec. In a finishing step subsequent to the step illustrated in FIG. 3, the nonwoven fabric having been obtained under these conditions was guided to pass through a heat treatment chamber (not shown) having a length of 1.8 m in the machine direction MD at a velocity of 20 m/min and thereby the short fibers 11 were further infused together. Within this heat treatment chamber, hot air at a temperature of 138° C. was circulated at a velocity of 0.7 m/sec. In this regard, respective temperatures of the first and second air jets 911, 921 at the first manifold 910 and the second manifold 920 are preset temperatures of hot air supplied to the respective manifolds from upstream thereof and the temperatures of the first and second air jets 911, 921 being ejected toward the short fibers which are inevitably lower than the preset temperatures were not measured.

TABLE 1 indicates measurement result of area ratio of void regions, loose passage permeation time, bulk recovery rate and average fiber angle obtained with a suction rate of the second suction box 925 fixed at 5 m/sec and an airflow rate of the second air jets changed between 4.0 to 8.3 L/min.

TABLE 1

| Airflow rate of second air jets (L/min) | Area ratio of void regions (%) | Loose passage permeation time (s/40 ml) | Bulk recovery rate (%) | Average fiber angle at apex of ridge (degrees) |
| --- | --- | --- | --- | --- |
| 4.0 | 2.1 | 28.4 | 52 | 71.8 |
| 4.3 | 2.4 | 19.2 | 52 | |
| 4.6 | 2.7 | 14.2 | 55 | |
| 5.0 | 3.3 | 11.1 | 55 | |
| 5.3 | 3.9 | 8.7 | 60 | |
| 5.6 | 4.1 | 9.4 | 66 | |
| 6.0 | 4.5 | 8.7 | 66 | |
| 6.3 | 4.9 | 8.0 | 85 | |
| 6.6 | 5.0 | 8.5 | 92 | 71.3 |
| 6.9 | 6.0 | 6.7 | 93 | |
| 7.3 | 6.0 | 6.8 | 92 | |
| 7.6 | 6.1 | 7.8 | 80 | |
| 7.9 | 6.2 | 6.7 | 95 | |
| 8.3 | 6.3 | 8.1 | 96 | |

Figure 5:
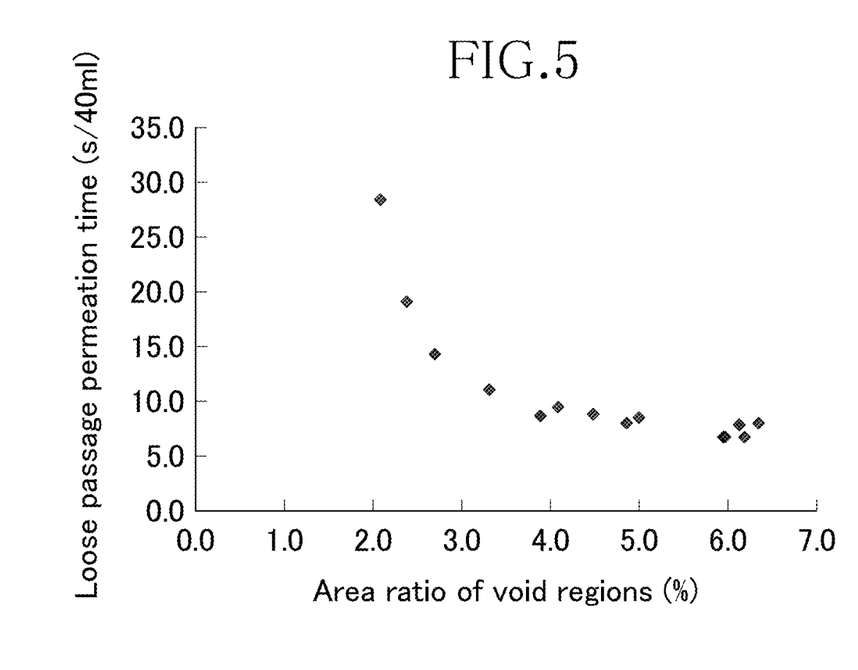
FIG. 5 A graphic diagram plotting area ratio of void regions versus loose passage permeation time.

FIG. 5 plots a relationship between the area ratio of void regions and the loose passage permeation time both indicated in TABLE 1. In the nonwoven fabric 1 according to this invention, the area ratio of the void regions plotted in FIG. 5 is at least 3.5% and such nonwoven fabric 1 assures the loose passage permeation time to be shortened. Preferably, the nonwoven fabric 1 having such an advantageous effect has the bulk recovery rate of at least 60% and the average fiber angle at apices of the respective ridges 6 of 75° or less.

Figure 6:
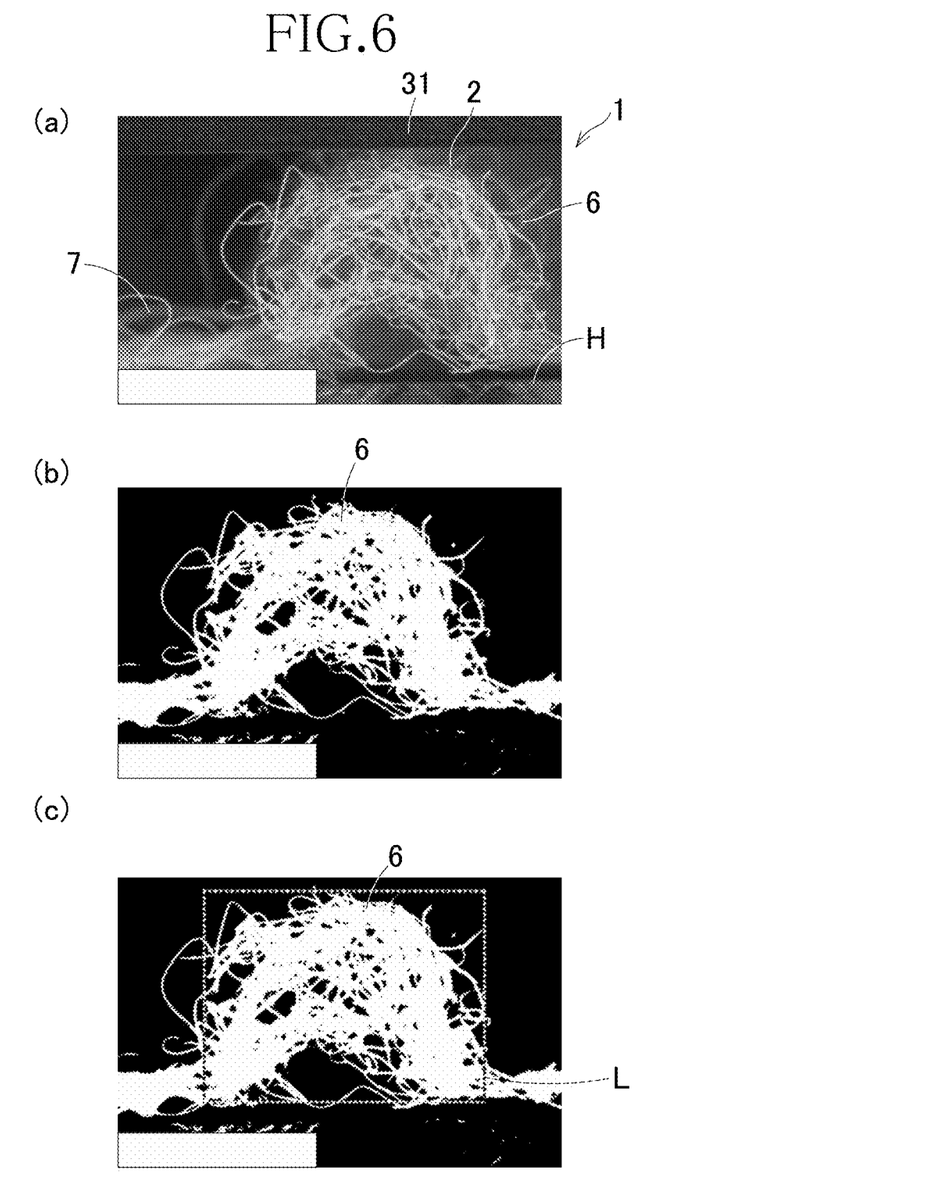
FIG. 6 Photographs (a), (b) and (c) illustrating procedures to measure area ratio of void regions.

FIG. 6 illustrates measurement procedures for the area ratio of the void regions in the respective ridges 6 of the nonwoven fabric obtained by following the steps illustrated in FIGS. 3 and 4 by means of a series of photographs (a) through (c). The procedures will be described below. In this regard, the photograph (a) in FIG. 6 is identical to the photograph in FIG. 2.

A. Preparation of Test Pieces for Measurement:

(1) The nonwoven fabric to be measured is cut by Replacement Blade HA-100 for Cutter Knife HA-7B (Trade Name) manufactured by Kokuyo CO., LTD. to prepare a test piece having a cross-section in the cross direction CD and this test piece is placed on a horizontal surface H of the measurement board.

(2) An acrylic plate (not shown) is placed on the top side 2 of the test piece and then a weight (not shown) is placed on the acrylic plate to subject the test piece to a load of 0.6 g/cm$^2$.

(3) Digital Microscope VHX-100 manufactured by Keyence Corporation is used to obtain photographs of 50-fold magnifications showing the cross-section of the test piece (See FIG. 2 and FIG. 6(a)).

B. Measurement of Sectional Area of Ridges and Area Ratio of Void Regions:

(1) Configuration Analysis Soft USB DEGITAL SCALE is used to read the photographic image having been prepared in the above-mentioned step A.

(2) The image is called up and binarized at a histogram value set to 80 (See FIG. 6(b)).

(3) One of the ridges in the image is specified as the ridge to be observed and this ridge is surrounded by a rectangular line L including one side falling into line with the horizontal surface H as illustrated (See FIG. 6(c)).

(4) The specified ridge is subjected to image analysis to calculate the area $S_1$ of a whitened section in which the short fibers close up together.

(5) The specified ridge is subjected to image analysis to calculate the area $S_2$ of a blackened section (i.e., the section in which none of the short fibers are present) above the horizontal surface H.

(6) The void region's cross-sectional area and the area ratio of void regions are calculated by the following formulae:

Void region's cross-sectional area=$S_1+S_2$

Area ratio of void regions=$S_2/(S_1+S_2)$

Measurement procedures for loose passage permeation time in TABLE 1:

(1) The nonwoven fabric to be measured is cut to obtain a test piece of 100×100 mm.

(2) Two hollow cylinders each having an inner diameter of 52 mm are stacked one on another and the test piece is placed between these two hollow cylinders. To prevent the test piece from bending, 30 mesh net having a thickness of 0.3 mm and made of synthetic resin underlies test piece.

(3) 40 ml of artificial loose passage is poured into the upper hollow cylinder for 5 seconds. Composition of artificial loose passage is cellulose:bentonite:water=3.3:6.7:90.

(4) A time elapsed from a time point at which pouring of the artificial loose passage starts to a time point at which permeation of the artificial loose passage ceases and a portion thereof is immobilized on the top side of the test piece is measured as the loose passage permeation time.

In this regard, a weight difference of the test piece before and after the measurement of the loose passage permeation time calculate as residual amount of loose passage. In TABLE 1, this residual amount of loose passage on the nonwoven fabric having the area ratio of void regions in a range of 2.1 to 6.3% is maintained virtually constant in a range of 4 to 5 g.

Measurement procedures for bulk recovery rate in TABLE 1:

(1) The nonwoven fabric to be measured is cut in 100×100 mm to obtain a test piece for measurement and this test piece is placed on the horizontal surface.

(2) An acrylic plate having thickness $T_0$ is placed on the surface of the test piece and a weight is placed on the acrylic plate to subject the test piece to a load of 3 g/cm$^2$, then such assembly is left at rest for 3 minutes.

(3) Then, a dial gauge is used to measure a total thickness $T_1$ of the test piece and the acrylic plate from above the acrylic plate.

(4) Now a weight is added to subject the test piece to a load 20 g/cm$^2$ and left at rest for 3 minutes. Thereafter the dial gauge is used to measure a total thickness $T_2$ of the test piece and the acrylic plate.

(5) After the load to the test piece is reduced to 3 g/cm$^2$ and left at rest for 5 minutes, the dial gauge is used to a total thickness $T_3$ of the test piece and the acrylic plate.

(6) A bulk recovery rate of the test piece is calculated by a following formula.

Bulk recovery rate(%)=$(T_3-T_0)/(T_1-T_0)\times100$

Figure 7:
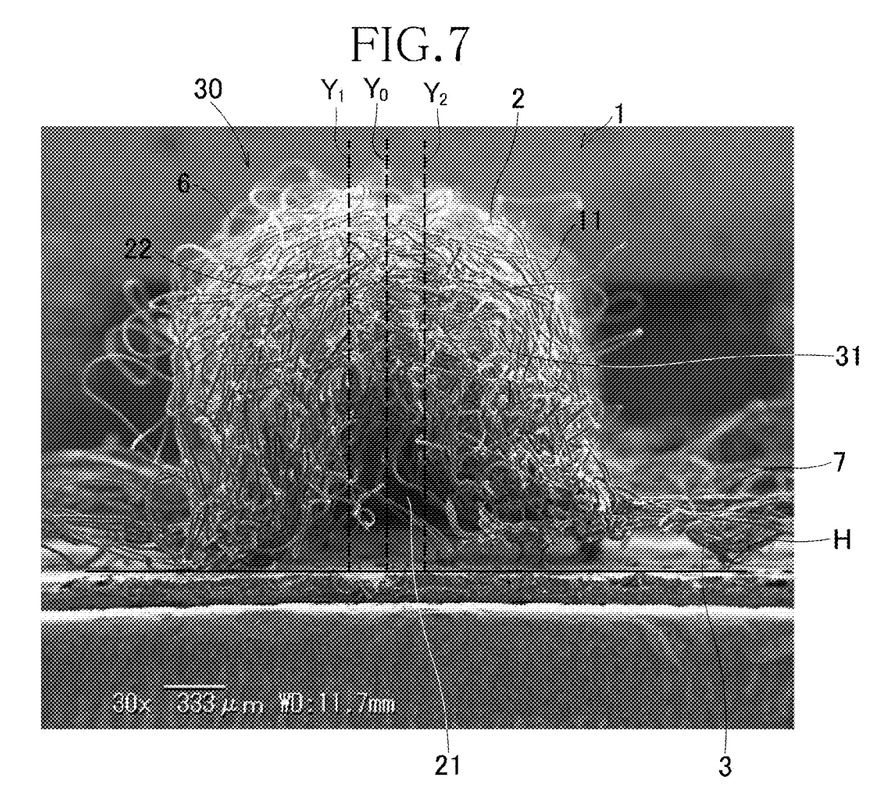
FIG. 7 A photograph showing cross-section of the nonwoven fabric.
Figure 8:
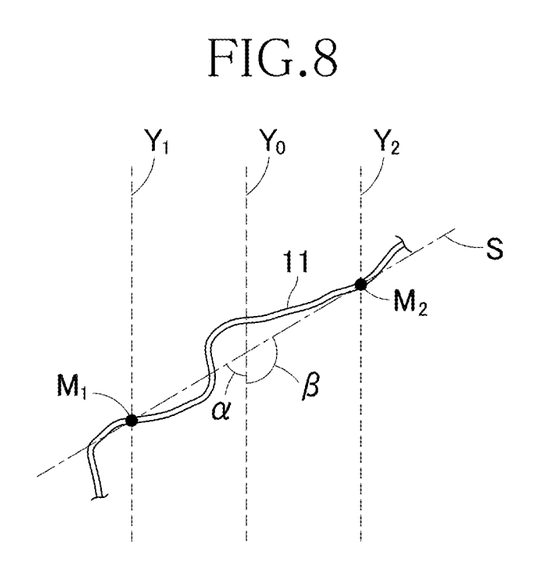
FIG. 8 A diagram schematically illustrating a part of cross-section of nonwoven fabric.

FIG. 7 is a photograph showing the cross-section of the nonwoven fabric and FIG. 8 is a diagram schematically illustrating a portion of this cross-section. In reference to these photograph and schematic diagram, the measurement procedures for the average fiber angle in TABLE 1 will be described hereunder.

(1) The nonwoven fabric to be measured, for example, the nonwoven fabric 1 illustrated in FIG. 1 is cut to obtain a test piece 30 for measurement of 100×100 mm and after the test piece 30 is heated at 70° C. for 30 minutes, wrinkles and/or rucks developed in the course of handling the test piece 30 are smoothed to obtain the test piece 30 as flat as possible.

(2) Standard Replacement Blade HA-7B for Cutter Knife HA-7B (Trade Name) manufactured by Kokuyo CO., LTD. is used to cut the test piece 30 in the cross direction to prepare a cut surface 31 (See FIG. 7) and this test piece 30 is placed on a horizontal surface.

(3) The cut surface 31 is observed by an electronic microscope (Real Surface View Microscope VE-7800 manufactured by Keyence Corporation) and a macro photograph of 30 magnifications (See FIG. 7) of this cut surface 31. In photographing, an overall height of the ridge in the test piece is brought in view.

(4) On the macro photograph of the image obtained in this manner, a horizontal line H coinciding with the horizontal surface and a vertical reference line $Y_1$ passing the apex of the ridge 6 and orthogonally crossing the horizontal surface are drawn.

(5) In addition, two vertical auxiliary lines $Y_1$, $Y_2$ extending on both sides and in parallel to the vertical reference line $Y_0$ so as to be spaced from the vertical reference line $Y_0$ by 100 μm.

(6) As illustrated in FIG. 8, intersection points between the respective short fibers with these two auxiliary lines $Y_1$, $Y_2$ are marked by $M_1$, $M_2$.

(7) The marks $M_1$, $M_2$ on these two auxiliary lines $Y_1$, $Y_2$ are connected with each other by a straight line S and crossing angles α, β between the straight line S and the vertical reference line $Y_0$ are measured. Of α and β, the smaller crossing angle is obtained as the fiber angle θ.

(8) The fiber angles are obtained for all the short fibers 11 and an arithmetic mean value of these fiber angles is designated as the average fiber angle $θ_m$.

REFERENCE SIGNS LIST 1 nonwoven fabric
2 top side
3 back side
6 ridges
7 troughs
11 short fibers
21 highly void regions
100 web
200 support means (belt)
901 preliminary treatment step (first step)
902 second step
911 first air jets
921 second air jets
A length direction
B width direction
C thickness direction
MD machine direction
CD cross direction
$\theta_m$ average fiber angle

The invention claimed is:

1. A nonwoven fabric, comprising:
   short fibers fused together,
   a top side and a back side,
   wherein
   the top side is formed with
      a plurality of ridges extending in parallel to one another in a first direction, and
      a plurality of troughs each defined between a corresponding pair of the adjacent ridges and extending in the first direction,
   in a cross-section of the nonwoven fabric taken in a second direction orthogonal to the first direction with the back side placed on a horizontal plane, the nonwoven fabric has highly void regions larger than interstices among the short fibers,
   the highly void regions are formed between the back side of the ridges and the horizontal plane,
   the short fibers at least in the vicinities of apices of the ridges slope downward to extend in a thickness direction of the nonwoven fabric,
   in the cross-section of the nonwoven fabric, an area ratio of highly void regions defined by a ratio of a first sum to a second sum is at least 3.5%, wherein
      the first sum is a sum of (i) an area occupied by interstices among the short fibers in the cross-section of the ridges and (ii) a cross-sectional area of the highly void regions, and
      the second sum is a sum of (i) the cross-sectional area of the ridges and (ii) the cross-sectional area of the highly void regions, and
   an elastic height recovery rate of the ridges as measured after the top side has been subjected to a load of 20 g/cm$^2$ for 3 minutes and then left in rest for 5 minutes is at least 60%.

2. The nonwoven fabric defined by claim 1, wherein, in the cross-section, an average value of crossing angles between a reference line passing an apex of each ridge perpendicularly to the horizontal plane and the short fibers is 75° or less.

3. The nonwoven fabric defined by claim 1, wherein, in the cross-section, the area ratio of highly void regions is in a range of 3.5 to 25.0%.

4. The nonwoven fabric defined by claim 1, wherein an elastic height recovery rate of the ridges as measured after the top side has been subjected to a load of 20 g/cm$^2$ for 3 minutes and then left in rest for 5 minutes is at least 85%.

5. The nonwoven fabric defined by claim 1, wherein
   the nonwoven fabric has a mass per unit area in a range of 10 to 80 g/m$^2$,
   the short fibers have fineness in a range of 1 to 11 dtx, and a fiber length in a range of 20 to 80 mm, and
   the short fibers are hydrophilic.

6. The nonwoven fabric defined by claim 1, wherein
   each of the short fibers is conjugate fibers formed from first and second thermoplastic synthetic resins respectively having different fusion temperatures, and
   the short fibers are fused together through an intermediary of the first thermoplastic synthetic resin having the fusion temperature lower than that of the second thermoplastic synthetic resin.

7. A method of manufacturing the nonwoven fabric defined by claim 1, said method comprising:
   (1) a first step, as a preliminary treating step including:
      placing a web, which is formed from short fibers of thermoplastic synthetic resin and has a top side and a back side, on an air-permeable support member,
      feeding the web in a machine direction under suction by a first suction member exerted from below the support, and
      ejecting first preheated air jets having an airflow rate three times or less of a suction volume of the first suction member to the web in a thickness direction of the web from the top side to the back side so as to compress the web in the thickness direction and simultaneously to fuse the short fibers together; and
   (2) a second step including:
      feeding the web placed on the support member further in the machine direction under suction by a second suction member exerted from below the support member, and
      ejecting second air jets having an airflow rate three times or more of a suction volume of the second suction member, from a plurality of nozzles arranged in a direction orthogonal to the machine direction, to the web in the thickness direction from the top side to the back side so that the second air jets are partially reflected on the support member and form
         a plurality of ridges extending in the machine direction in parallel to one another,
         a plurality of troughs defined between the adjacent ridges and extending in the machine direction, and
         between the back side in the ridges and the support member, highly void regions larger than interstices among the short fibers in the ridges.

* * * * *